United States Patent [19]

Benabid et al.

[11] Patent Number: 5,800,474
[45] Date of Patent: Sep. 1, 1998

[54] METHOD OF CONTROLLING EPILEPSY BY BRAIN STIMULATION

[75] Inventors: Alim L. Benabid, Meylan; Christian Marescaux, Strasbourg, both of France

[73] Assignee: Medtronic, Inc., Minneapolis, Minn.

[21] Appl. No.: 742,841

[22] Filed: Nov. 1, 1996

[51] Int. Cl.$^6$ .............................. A61N 1/32; A61N 1/05; A61N 1/372

[52] U.S. Cl. .............................. 607/45; 607/72; 607/48

[58] Field of Search .............................. 607/45, 46, 48, 607/58, 72

[56] References Cited

U.S. PATENT DOCUMENTS

| | | | |
|---|---|---|---|
| 3,850,161 | 11/1974 | Liss | 607/45 |
| 3,918,461 | 11/1975 | Cooper | 607/45 |
| 5,025,807 | 6/1991 | Zabara | 607/45 |
| 5,299,569 | 4/1994 | Wernicke et al. | 607/45 |
| 5,474,547 | 12/1995 | Aebischer et al. | 128/898 |

OTHER PUBLICATIONS

Mark Hallett, "The Plastic Brain," *Annals of Neurology*, vol. 38,Nno. 1, Jul. 1995.

C.W. Olanow et al., "The effect of Deprenyl and Levodopa on the Progression of Parkinson's Disease"*Ann Neurol.* 1995;38:771–777

Stanley J. Appel, "A Unifying Hypothesis for the Cause of Amyotrophic Lateral Slcerosis, and Alzheimer Disease, " *Ann Neurol.* 1981;10499–505.

J.T. Greenamyre, "Glutamate–dopamine Interactions in the Basal Ganglia: Relationship to Parkinson's Disease, "*J. Neural Transm* [GenSect]1993;255–269.

*Primary Examiner*—William E. Kamm
*Assistant Examiner*—Carl H. Layno
*Attorney, Agent, or Firm*—Curtis D. Kinghorn; Harold R. Patton

[57] ABSTRACT

A method of preventing seizures as experienced by persons with Epilepsy. High frequency electrical stimulation pulses are supplied to the subthalamic nucleus thereby blocking neural activity in the subthalamic nucleus and reducing excitatory input to the substantia nigra which leads to a reduction in the occurrence of seizures.

2 Claims, 1 Drawing Sheet

METHOD OF CONTROLLING EPILEPSY BY BRAIN STIMULATION

BACKGROUND OF THE INVENTION

1. Field of the Invention

This invention relates to brain stimulation techniques, and more particularly relates to such techniques for treating epilepsy.

2. Description of Related Art

Epileptic seizures are the outward manifestation of excessive and/or hyper synchronous abnormal activity of neurons in the cerebral cortex. Seizures are usually self limiting. Many types of seizures occur. The behavioral features of a seizure reflect function of the portion of the cortex where the hyper activity is occurring. Seizures can be generalized, appearing to involve the entire brain simultaneously. Generalized seizures can result in the loss of conscious awareness only and are then called absence seizures (previously referred to as "petit mal"). Alternatively, the generalized seizure may result in a convulsion with tonic-clonic contractions of the muscles ("grand mall" seizure). Some types of seizures, partial seizures, begin in one part of the brain and remain local. The person may remain conscious throughout the seizure. If the person looses consciousness the seizure is referred to as a complex partial seizure.

Researchers have developed several lines of evidence in studies with animals to demonstrate the existence of a system which can control the propagation and/or the generation of different kinds of seizures. The involvement of the substantia nigra, a particular portion of the brain considered to be part of neural circuitry referred to as the basal ganglia, was first suggested by Gale (*Fed. Proc.* 44, 2414–2424, 1985). Considerable evidence has been generated through research to support this observation and was reviewed by Depaulis, Vergnes and Marescaux (Progress in Neurobiology, 1994, 42:33–52). Researchers have shown that the inhibition of the substantia nigra will increase the threshold for seizure occurrence in experimental animal models of epilepsy.

Neuroscientist now have a better understanding of the neural connections that make up the basal ganglia. These connections are reviewed by (Alexander, Crutcher, and DeLong, "Basal gnaglia-thalamocortical circuits:parallel substrates for motor, oculomotor, 'prefrontal' and 'limbic' functions." *Prog. Brain Res.* 85:119–146.). The substantia nigra receives input from the subthalamic nucleus which is excitatory and involves glutamate as the neurotransmitter conveying information at the synapse. Bergman et al. have shown that a lesion of the subthalamic nucleus will reduce the inhibitory output of the internal segment of the globus pallidus and substantia nigra reticulata (H. T. Bergman, T. Wichmann, and M. R. DeLong, 1990, *Science*, 249:1436–1438).

Benabid et al. (*The Lancet*, Vol 337:Feb 16, 1991, pp 403–406) have shown that stimulation of the Vim nucleus of the Thalamus will block tremor. In this instance, stimulation at frequencies around 100 to 185 pulses per second accomplishes the same physiological response as a lesion of this region. Benabid's research team has extended this work to stimulation of the subthalamus in order to help reduce symptoms of motion disorders ("Vim and STN Stimulation in Parkinson's disease", *Movement Disorders*, Vol 9, *Supplement* 1(1994); "Effect on Parkinsonian signs and symptoms of bilateral subthalamic nucleus stimulation", *The Lancet*, Vol 345, Jan. 14, 1995.)

SUMMARY OF THE INVENTION

A preferred form of the invention can treat a movement disorder resulting in abnormal motor response by means of an implantable signal generator and an implantable electrode having a proximal end coupled to the signal generator and having a stimulation portion for therapeutically stimulating the brain. The electrode is implanted in the brain so that the stimulation portion lies in the subthalamic nucleus. The signal generator is operated to pulse the electrode at a predetermined rate and amplitude that is sufficient to block activity of the subthalamic nucleus and thereby reduce the excitation of the substantia nigra by the subthalamic nucleus. The reduction in excitation of the substantia nigra reduces the occurrence of seizures.

By using the foregoing method, the occurrence of epileptic seizures in persons with epilepsy is reduced beyond the level attainable by prior art methods or apparatus.

BRIEF DESCRIPTION OF THE DRAWINGS

These and other advantages and features of the invention will become apparent upon reading the following detailed description and referring to the accompanying drawings in which like numbers refer to like parts throughout and in which.

DESCRIPTION OF THE PREFERRED EMBODIMENTS

Figure 1:
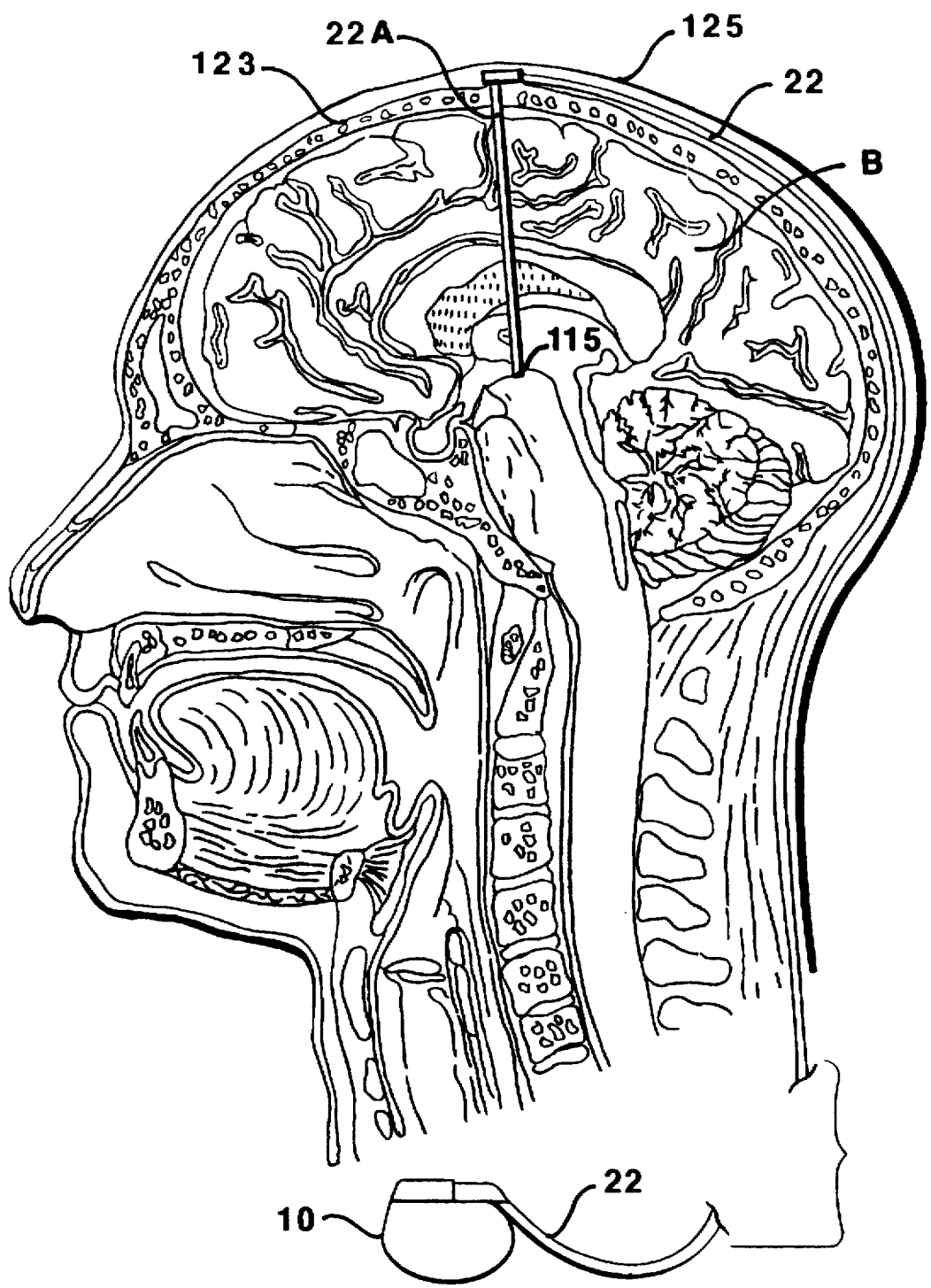
FIG. 1 is a diagrammatic illustration of a stimulation electrode implanted in a brain according to a preferred embodiment of the present invention and a signal generator coupled to the electrode.

Referring to FIG. 1, a electrical signal generating system or device 10 made in accordance with the preferred embodiment may be implanted below the skin of a patient. Device 10 may be implanted beneath the clavicle on the chest or in the abdomen. Device 10 is preferably an implantable pulse generator (IPG). An example of such an IPG is Model 7424 manufactured by Medtronic, Inc. under the trademark Itrel II which is incorporated by reference. Device 10 may also be a pulse generating system that is located outside the body. In addition, device 10 may also be a generator or electrical signals that are not pulses, including but not limited to signals that are sinusoidal, stepped or trapezoidal.

A lead 22A is positioned in the brain (B) to stimulate a specific site in the brain (B). Lead 22A may take the form of any of the leads used for deep brain stimulation such as any of the leads sold with the Model 7424. Lead 22A is coupled to device 10 by a conventional conductor 22.

The distal end of lead 22A terminates in four stimulation electrodes generally designated 115 implanted into a portion of the basal ganglia of the brain. Implantation may be done by conventional stereotactic surgical techniques. Although four electrodes is the preffered number, other numbers of electrodes, such as two or three or more than four may be used. Each of the four electrodes is connected to device 10 through lead 22A and conductor 22.

Lead 22A is surgically implanted through a hole in the skull 123 and conductor 22 is implanted between the skull and the scalp 125 as shown in FIG. 1. Conductor 22 is electrically joined to device 10.

Device 10 is programmed to produce stimulation pulses having a repetition rate of about 10–2500 HZ. At these frequencies, stimulation of the subthalamic nucleus is blocked. This has the effect of reducing the excitatory input conveyed to the substantia nigra by the axons projecting from the subthalamic nucleus. Reducing the excitation of the substantia nigra reduces the chance that the user will have a seizure.

By using the foregoing techniques, the number of seizures experienced by persons with epilepsy can be controlled with a degree of accuracy previously unattainable.

Those skilled in the art will recognize that the preferred embodiment may be altered or amended without departing from the true spirit and scope of the invention, as defined in the accompanying claims.

We claim:

1. A method of therapeutically treating epilepsy resulting in a reduction in the occurrence of seizures comprising the steps of:

surgically implanting an implantable electrode in the brain, the implantable electrode having a proximal end and a stimulation portion, the electrode being implanted in the brain so that the stimulation portion of the electrode lies in the subthalamic nucleus of the brain;

providing an electrical signal generator;

coupling said proximal end of said electrode to said signal generator; and operating said signal generator at a predetermined stimulus repetition rate high enough to block activity of the subthalamic nucleus to reduce the excitatory input from the subthalamic nucleus to the substantia nigra there by reducing the occurrence of seizures.

2. A method, as claimed in claim 1, wherein said stimulus repetition rate is about 10–2500 Hz.

* * * * *